United States Patent [19]

Comte

[11] Patent Number: 4,640,983

[45] Date of Patent: Feb. 3, 1987

[54] CONDUCTOR DEVICE, PARTICULARLY FOR AT LEAST PARTIAL INSERTION IN A HUMAN OR ANIMAL BODY, COMPRISING A SPIRAL FORMED FROM AT LEAST ONE CONDUCTOR

[75] Inventor: Pierre-Andre Comte, Liestal, Switzerland

[73] Assignee: Institut Straumann AG, Waldenburg, Switzerland

[21] Appl. No.: 720,550

[22] Filed: Apr. 8, 1985

[30] Foreign Application Priority Data

Apr. 9, 1984 [CH] Switzerland .......................... 1773/84

[51] Int. Cl.⁴ .............................................. H01B 5/10
[52] U.S. Cl. ................................. 174/119 R; 128/784; 174/128 R; 174/130
[58] Field of Search ............... 174/119 R, 128 R, 130, 174/69, 126 S, 128 S; 128/419 P, 784, 785, 786

[56] References Cited

U.S. PATENT DOCUMENTS

| | | | |
|---|---|---|---|
| 2,321,021 | 6/1943 | Dyer, Jr. .......................... | 174/128 R |
| 2,978,530 | 4/1961 | Braeckman ...................... | 174/119 R |
| 3,333,045 | 7/1967 | Fisher et al. ...................... | 174/130 |
| 3,367,339 | 2/1968 | Sessions ........................... | 128/419 P |
| 3,572,344 | 3/1971 | Bolduc ............................. | 128/419 P |
| 3,596,662 | 8/1971 | Bolduc ............................. | 128/418 |
| 3,760,812 | 9/1973 | Timm et al. ...................... | 174/130 X |
| 4,079,187 | 3/1978 | Fillunger et al. ................. | 174/128 S |
| 4,402,330 | 9/1983 | Lindemans ...................... | 128/419 P X |
| 4,458,695 | 7/1984 | Peers-Trevarton .............. | 128/419 P X |

FOREIGN PATENT DOCUMENTS

| | | | |
|---|---|---|---|
| 57877 | 8/1982 | European Pat. Off. ............ | 128/785 |
| 2820867 | 11/1979 | Fed. Rep. of Germany ... | 128/419 P |
| 8004757 | 2/1981 | Netherlands ........................ | 128/784 |

OTHER PUBLICATIONS

Schaldach, R.; "Fatigue Performances of Stimulating Electrodes"; (Biomedical Engineering); vol. 28, supplemental volume; May 1983.
Kaul, Tej K.; "Failure of Pacemaker Electrode Leads"; European Journal of Cardiology; 1979, 10/5; pp. 385–394.
Bisping, H. J.; "New Pacemaker Leads"; (Biomedical Engineering); vol. 25, Jul./Aug. 1980; pp. 170–175.

Primary Examiner—Arthur T. Grimley
Assistant Examiner—Morris H. Nimmo
Attorney, Agent, or Firm—Toren, McGeady and Goldberg

[57] ABSTRACT

A conductor device having at least one spiral which is formed from at least one conductor, each conductor consisting of wires which are stranded together to form a bundle. In addition, the wires belonging to a conductor can all consist of the same material or of different materials, one of which has a large breaking strength and the other one having high electric conductivity. The conductor device can connect, for example, in a heart pacemaker, the contact electrode inserted in the heart with an electric pulse generator. The conductor device provides a relatively high electric conductance with great flexibility, expandability, breaking strength and, in particular, fatigue resistance.

18 Claims, 8 Drawing Figures

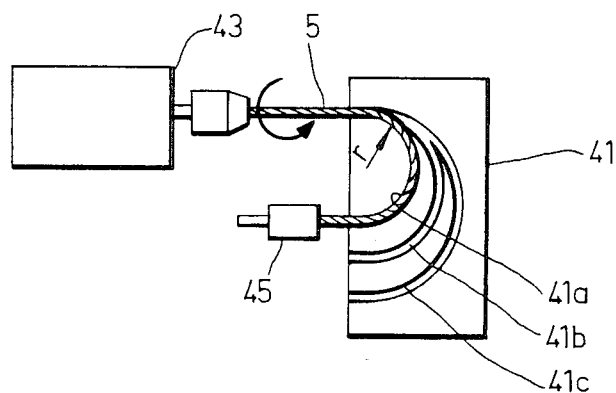
Fig.5
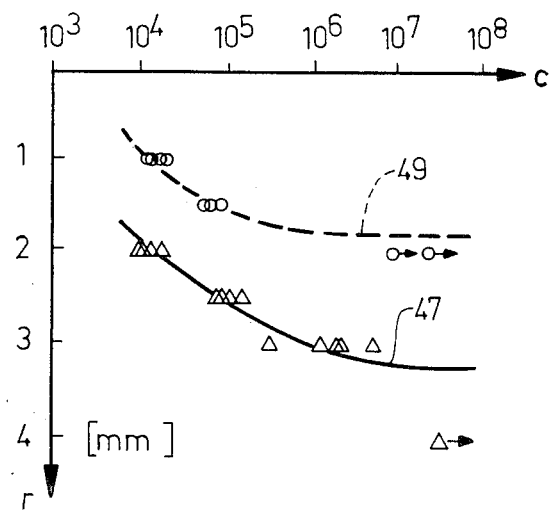
Fig.6
Fig.3
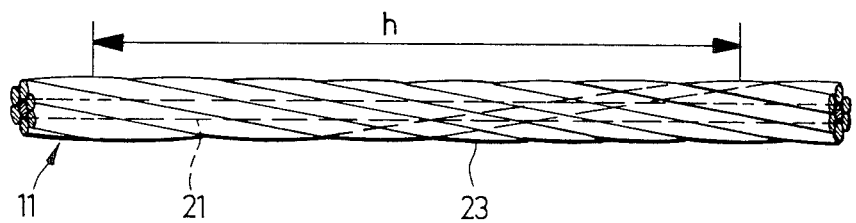

CONDUCTOR DEVICE, PARTICULARLY FOR AT LEAST PARTIAL INSERTION IN A HUMAN OR ANIMAL BODY, COMPRISING A SPIRAL FORMED FROM AT LEAST ONE CONDUCTOR

The present invention is directed to a conductor device which is particularly adapted for at least partial insertion in a human or animal body.

The conductor device is intended for applications in which, in addition to the largest possible electric conductance, the conductor device also has good deformability, particularly bending ability, and a high fatigue resistance. As used hereinafter, the term "fatigue resistance" signifies the resistance to alternating deformations, such as expansions, stretching and, above all, bending, as well as torsion.

The conductor device is particularly provided to be completely or at least partly inserted in a human or animal body and to form a part of a stimulation and/or measuring device. The conductor device is provided, for example, for heart stimulation, i.e., for use as a conductor and/or electrode for a heart pacemaker. But it can also be used for other types of neuro, muscular or bone stimulation. In addition, the conductor device can also serve to feed electric signals produced by body cells to a measuring device.

The conductor device can serve as a conductor in order to conduct an electric current from a current source to an activator arranged in a part of the body or from a sensor arranged in a part of the body to a measuring device. In so doing, the activator or sensor can be formed by means of a separate member connected at the one end of the conductor device or by means of the blank insulated end of the conductor or conductors of the conductor device. Possibly a longitudinal section of the spiral or the entire spiral of the conductor device can be blank, as well, and can serve as an activator or sensor. At least in the case where at least a part of the conductor or conductors serves as activator or sensor, the conductor device forms an electrode.

A conductor device with a conductor is known from U.S. Pat. No. 3,572,344 which has a mandrel, arbor, spindle, spike, core bar, or the like, consisting of insulating material, around which several leads are helically wound, which leads, in turn, consist, in each instance, of a core of insulating material and a conductor wound around the latter. The various leads are all connected at one end of the electrode with an angled, canted contact and, at the other conductor end, they are all connected with a pin determined for the connection with a device.

In addition, conductor devices provided for heart pacemakers comprising a two-core, bifilar, or twin-lead cable and two laterally projecting, pin-shaped contacts are known from U.S. Pat. No. 3,596,662. The cable has two wire spirals extending next to one another which are enclosed by an insulating sheathing or jacket and are also filled on their inside with insulating material.

But these known conductor devices, in which the spiral contains a core of insulating material, have relatively poor bending and expanding abilities and only a limited fatigue resistance, as well as relatively large cross-sectional dimensionings. Moreover, in comparison with their bending resistances, fatigue resistances and cross-sectional dimensionings, these conductor devices have only a relatively low electrical conductance.

In medical practice, at present, conductor devices having an electrically conducting spiral or two coaxial spirals are primarily used for heart pacemakers, wherein the spiral or outer spiral, respectively, is provided with an insulating material and there is an open cavity within the spiral or inner spiral, respectively. Each spiral is formed from a single wire or from adjacently extending wires in the manner of a multiple thread. These known conductor devices have wires consisting, for example, of cobalt alloys or stainless, rust-resistant steel. But, despite the relatively great strength of these materials, breakage or fractures occur in these conductor devices relatively frequently, chiefly fatigue fractures during bending with small radii or curvature. In addition, these materials have only a relatively low electric conducting capability. Therefore, if a spiral is formed from only a single conductor, it has a relatively high electrical resistance. The spirals of these known conductor devices were therefore usually formed from several conductors extending adjacent to one another in the manner of a multiple thread in order thereby to reduce the electrical resistance or increase the conductance, respectively. But if one increases the quantity of conductors making up the spiral when the conductor and spiral diameters are constant, the pitch, ascending gradient or slope of the spiral becomes larger and the fatigue resistance accordingly becomes lower. Reference should be made here, for example, to the publication "Fatigue Performances of Stimulating Electrodes" by P. Comte, E. Gysin and Th. Baehny, in *Biomedizinische Technik*, Vol. 28, Supplementary Vol., May 1983. In addition, publication "Failure of Pacemaker Electrode Leads" by T. K. Kaul, G. D. Green and W. H. Bain, in *European Journal of Cardiology*, 1979, 10/5, pp. 385–394, contains examination test results on the service life or durability of various known conductor devices of heart pacemakers. According to the latter publication, electrodes inserted in patients break at a rate of 1 to 7.3% per year. Since such breakage can, under certain circumstances, cause the death of the patient concerned, breakage rates of this magnitude naturally constitute a considerable disadvantage.

Conductor devices are also known already whose spirals are formed, for example, of three adjacently extending conductors, each of which is formed from a compound, composite, or compound-wound wire consisting of silver and of the cobalt-nickel alloy known by the commercial name MP 35 N. The sheathing of the wire is formed from six segments consisting of said cobalt-nickel alloy, which segments enclose a core of silver and are securely connected with the latter and with one another. Reference should be made here to the publication "Neue Schrittmachersonden—ein Bericht aus Montreal" by H. J. Bisping, in *Biomedizinische Technik*, Vol. 25, 1980, pp 170–175.

However, investigations of conductor devices with spirals formed from such compound wires show that these spirals are already plastically deformed by means of relatively slight deformations. Therefore, when implanting such a conductor device in the body of a patient, permanent bends or even kink-type deformations can occur. The fatigue resistance is substantially reduced in such plastically deformed places.

SUMMARY OF THE INVENTION

The objective of the present invention is to provide a conductor device which, with the smallest possible outer diameter of the spiral, has a high fatigue resistance and a relatively high electrical conductance or low electrical resistance, respectively.

This objective is met by means of a conductor device which is constructed according to the invention, particularly for at least partial insertion in a human or animal body and for use with a pacemaker. The conductor device in accordance with the invention is formed to comprise at least one spiral formed from at least one electrical conductor, wherein the conductor is formed from at least two wires which are held together. For example, the spiral, or each spiral, respectively, can have only one or at least two conductors extending next to one another in the manner of a multiple thread, wherein there are preferably, at most, four or five conductors per spiral. The conductor, or each conductor, respectively, consists of at least two wires which are held together and, together, form a bundle, wherein there are advisably at least three, preferably at least five and, for example, at least seven wires per conductor. In an advantageous embodiment, the conductor, or each conductor, is blank, wherein, however, the spiral can be sheathed, at least in a partial area of its length, with an electrically insulating sheathing. Moreover, the conductor device can have only one spiral or two or possibly even more than two spirals which, in each instance, are formed from at least one conductor and are insulated from one another, wherein the spirals are advisably arranged coaxially relative to one another.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there are illustrated and described preferred embodiments of the invention.

DESCRIPTION OF THE DRAWINGS

In the drawings:

FIG. 3 is a view of a single, unwound, i.e., linearly extending, conductor;

FIG. 5 is a schematic view of a testing device for testing the fatigue resistance;

FIG. 6 is a diagram illustrating the relationship between the radius of curvature and the fatigue resistance of the spirals;

DETAILED DESCRIPTION OF THE PREFERRED EMBODIMENTS

Figure 1:
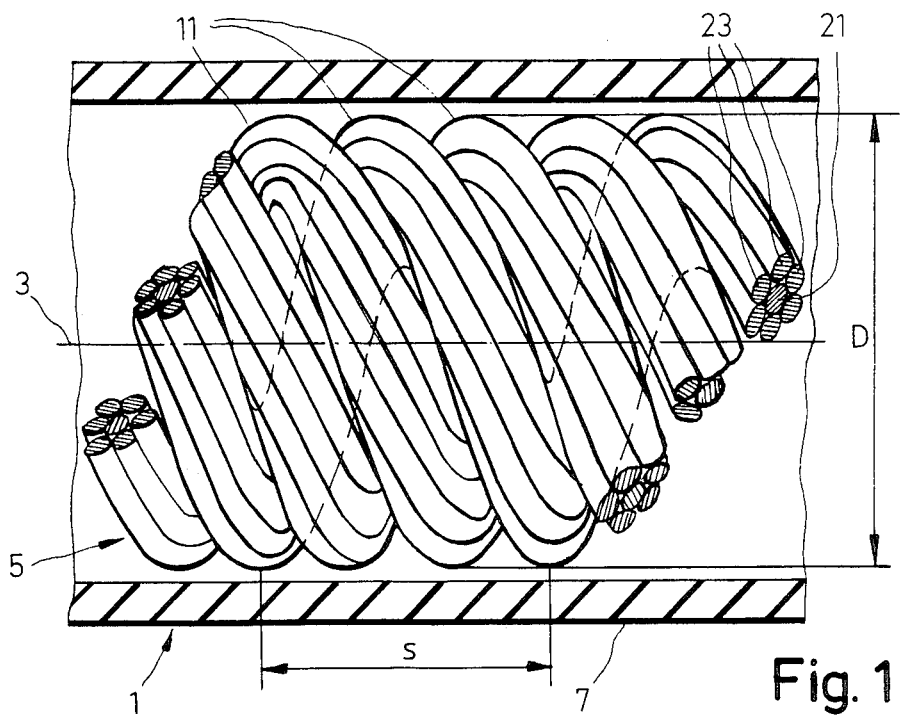
FIG. 1 is a longitudinal section of a conductor device, wherein the sheathing is shown in section and the spiral is shown in front view.

Referring now to the drawings, the invention is shown as comprising an oblong, elongate, bendable, electric conductor device 1, of which a longitudinal section is shown in FIG. 1, having an electrically conducting spiral 5 extending around a longitudinal axis 3 and an electrically insulating sheathing 7 which sheathes the latter in a close fitting manner or with some play. The sheathing 7 consists of an electrically insulating, rubber-elastic, favorably bendable and biologically compatible material, e.g., an elastomer on a polyurethane or silicon base. The spiral 5 has n conductors 11, that is, at least one and preferably at least two, and advisably at most five and preferably at most, four conductors 11. If the spiral has more than one conductor 11, then these together form a single-layer winding or coil and extend next to one another in the manner of a multiple thread so that, in an undeformed conductor device 1, the windings of the conductors 11 overlap one another in the axial projection and together form a cylindrical sheathing. In the embodiment of the conductor device shown in FIG. 1, three conductors 11 are shown by way of example which extend next to one another in the manner of a triple thread. The outer diameter of the spiral 5 or, more exactly, the diameter of its circular-cylindrical sheathing surface in an undeformed state, is designated D. The central inner area of the spiral 5 enclosed by the windings of the conductors 11 form a free, open cavity.

Each conductor 11 consists of at least two, advisably at least three, and preferably at least five, and at most, approximately 20 wires. In the embodiment shown in FIG. 1, each conductor 11 has seven wires 21, 23, as can be seen particularly clearly from FIG. 2. The wire 21 forms the core of the conductor 11. The other six outer wires are uniformly distributed around the wire 21. The wires 21, 23 have circular cross-sections and have a diameter d. Preferably, at least all of the wires 23 distributed around the core, or all of the wires 21, 23, in general, have diameters, so that each outer wire 23 contacts the central wire 21, as well as two other outer wires 23. Such a conductor 11, formed from seven wires, as viewed in cross-section with reference to its central axis, has a relatively uniform material distribution and a relatively round contour or outline. The largest cross-sectional dimensioning, i.e., of the enveloping diameter of a conductor 11, is designated a. The wires 23 are wound or twisted around the longitudinal axis of the conductor 11 and the wire 21. The winding direction or the twisting direction, respectively, or the wires 23 is opposed to the turning or rotating direction with which the conductors 11 extend around the axis 3, but it could also possibly be in the same direction as the turning direction of the conductors.

The pitch of the spiral 5, i.e., the lead or pitch s, is at least approximately equal to the product of the quantity of conductors 11 extending next to one another times the enveloping diameter of the conductors 11, i.e., at least approximately equal to the product na, and, for the embodiment shown in FIG. 1, it is at least approximately equal to the product 3a. The lead or pitch s of the conductors 11 is advisably at most 100% larger than the product na. The conductors 11 are, for example, according to FIG. 1, distributed and wound in such a way that the distance between adjacent windings of the conductors 11 are everywhere at least approximately equal in size. The adjacent windings of the conductors 11 can contact one another or can be separated by means of an intermediate space whose axially measured dimensioning is advisably at most approximately equal to the enveloping diameter a of a conductor 11 and is advantageously at most approximately 30% of the enveloping diameter a of the conductor 11.

Figure 2:
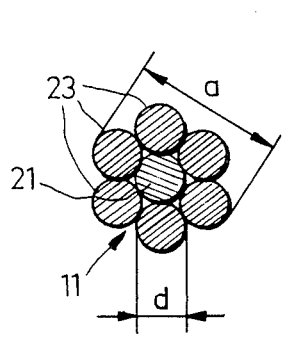
FIG. 2 is a cross-section through a conductor, in enlarged scale.

The winding length of the wires or, more precisely, the length of the portion of a conductor 11 occupied by one full winding of a wire 23, i.e., the lead or pitch of the wound or twisted together outer wires 23 is designated h in FIG. 3, showing a single, linearly extending conductor 11, and the quantity of wound wires 23 of a conductor is designated m, wherein m is equal to six in the conductors 11 shown in FIGS. 1–3. The winding length h is larger than the product of the quantity of wound wires 23 times the wire diameter, i.e., than the product md, and is advisably at least twice and preferably at least triple the product md. The winding length h can amount to approximately twenty to eighty times the wire diameter d. In addition, the winding length h is at least 25% and preferably at least 40% and at most 200% and preferably at most 100% of the unwound length of a winding of the conductor 11. The winding length h can be, e.g., approximately 50% to 80% of the unwound length of a winding of the conductor 11. For the sake of clarity, it should be noted that the unwound length of a winding of the conductor 11 signifies the average unwound length of such a winding.

In that the wires 23 are wound or twisted, respectively, around the axis of a conductor 11 and around the wire 21 forming its core, they are connected to form a bundle, i.e., a cable or twisted together thread. The wires 21, 23 belonging to the same conductor 11 are thus held together, wherein, however, the different wires 21, 23 are not rigidly connected together, but rather, only contact one another and can move with respect to one another, at least within certain limits.

If the conductor device 1 is determined for use as part of a heart pacemaker, a contact electrode, which connects the conductor, or conductors 11, with the tissue to be stimulated, can be arranged at its end on the heart side as an activator. The contact electrode is preferably provided with a sealing part which seals the interior of the sheathing 7 and, accordingly, also the cavity enclosed by the spiral 5, in a tight-fitting, air-tight, impervious manner, for example, a sleeve which encloses the end section of the sheathing 7 and is fastened at the latter. At the other end, the conductor device has a connection which is connectable at an electric pulse generator. For the possible constructions of the contact electrode and the connection, the cited literature and other prior art should be referred to. When the heart pacemaker is inserted, the spiral 5 connects the pulse generator with the contact electrode so as to conduct electrically. The conductor device 1 is, moreover, constructed in such a way that, from its end which is connectable at the pulse generator, a so-called "stylet", which is formed by means of a wire-shaped mandrel or which has such a mandrel, can be temporarily inserted in the cavity defined by the spiral 5 in order to insert the conductor device 1 in a patient. After removing the stylet, the cavity of the spiral can possibly also be sealed by means of a sealing part at its end determined for the connection at the pulse generator.

The wires 21, 23 are normally protected from contact with blood and other liquids, as well as from solid parts of the body of the patient in whom the conductor device is inserted, by means of the sheathing 7 and the sealing part sealing its interior at least at the end of the conductor device 1 at the heart side. However, since the conductors 11 could, under certain circumstances, come in contact with blood or other cells and tissues of the patient's body, for example, if the sheathing 7 is damaged, the wires forming the conductors 11 advisably consist of materials which are, at least to some extent, biologically compatible.

The outer diameter D of the spiral can, for example, amount to approximately 0.5 mm to 3 mm. At least in the case where the conductor device 1 belongs to a heart pacemaker, the outer diameter D of the spiral is advisably at most 1.5 mm and preferably at most 1 mm. The diameter d of the wires 21, 23 is advisably at most 10% and preferably at most 7% of the outer diameter D of the spiral 5. In addition, the wire diameter d is advisably at most 0.08 mm, preferably at most 0.06 mm and, for example, at least 0.02 mm to 0.06 mm.

The wires 21, 23 belonging to a conductor 11 can either all consist of the same, electrically conducting material or can consist of different materials. At least a part of the wires of a conductor 11 should consist of a material having, above all, good mechanical characteristics, such as a large elasticity limit, a large breaking strength or fracture resistance and, particularly, a large endurance strength or fatigue limit. Accordingly, the wires consisting of this material should be favorably elastically deformable and should be bendable particularly with small radii of curvature, without breakage occurring.

Materials satisfying these demands are, e.g., various cobalt containing alloys, such as the CoNiCrMoWFe alloy (standard ASTM F 563-78) supplied under the commercial name Syntacoben by Institut Straumann AG, Switzerland, the CoNiCrMoTi alloy (standards ISO 5832/6; ASTM F 562-78) supplied under the commercial name MP 35 N by The Standard Pressed Steel Co., U.S.A. and the CoCrFeNi alloy supplied under the commercial name Elgiloy by Elgin National Watch Co., U.S.A. Moreover, the wires, or a part of them, instead of being produced from these cobalt alloys, could also be produced from stainless steel, such as the Fe, Cr, Ni, Mo containing steel (standards ISO 5832/1; ASTM F 138-76) commercially available under the designation 316 L, or possibly from tungsten.

Of these materials, it is particularly the cobalt alloys and the stainless steel which have relatively low electric conducting abilities. For example, the electric conducting abilities of the cobalt alloys mentioned above lie in the order of magnitude of $10^6$ S/m. But it is easily possible to form each conductor from wires consisting of different materials. Each conductor can have at least one wire consisting of a first material with high breaking strength and at least one wire consisting of a second material with high electric conducting ability. The first material can be one of the cobalt alloys or stainless steel, mentioned above, for example. The second material can be silver or copper, for example, whose electric conducting ability amounts to $60 \cdot 10^6$ S/m and $57 \cdot 10^6$ S/m, respectively. Instead of silver or copper, gold, platinum or aluminum can also be considered as a second material. The material with the higher conducting ability can then have a lower breaking strength and endurance strength than the first material, i.e., the cobalt alloys and stainless steel.

In terms of conducting ability, tungsten lies between the cobalt alloys or stainless steel and silver or copper and can possibly be used, according to circumstances, as first or second material. Advisably, at least half, i.e., at least 50% and preferably 70% of the wires of a conductor consist of one of the first materials having a high strength, wherein, however, the reverse is also possible.

Figure 4:
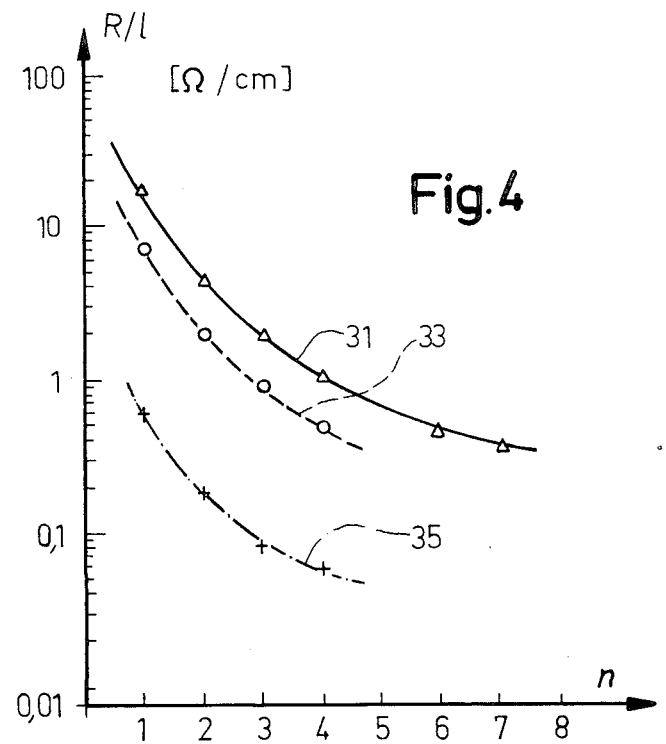
FIG. 4 is a diagram illustrating the dependence of the resistance per unit of length on the spiral on the quantity of conductors.

Investigations were carried out, among others, in which the resistance per length unit was measured for different variants of spirals. Some of the test results are illustrated in the diagram shown in FIG. 4. In FIG. 4, the variable n, i.e., the quantity of conductors from which a spiral is formed, is indicated on the abscissa. The resistance per length unit of the spiral, designated R/l, in Ohms per centimeter is plotted on the ordinate.

The outer diameter D of the spirals tested was 0.8 mm and the spirals were all wound as tightly as possible so that adjacent windings contacted each other at least approximately.

Curve 31 shows the dependence of the resistance per length unit of the spirals on the quantity of conductors for conductor devices, not according to the invention, in which the conductor, or each conductor, is formed from a single wire having a circular cross-section and with a diameter of 0.1 mm, wherein the wire consists of the cobalt alloy MP 35 N mentioned previously. Curve 33 shows the dependence of the resistance per length unit of the spirals for conductor devices, according to the invention, in which the conductor, or each conductor, respectively, is formed from seven wires consisting of cobalt alloy MP 35 N, which wires have circular cross-sections and a diameter d of 0.05 mm. Curve 35 is directed to conductor devices, according to the invention, in which the conductor, or each conductor, respectively, is formed from six wires consisting of the cobalt alloy MP 35 N with a diameter d of 0.05 mm and from a wire of copper with a diameter d of 0.06 mm. The copper wire forms one of the outer wires 23.

As can be seen in FIG. 4, the resistance in each of the three types of conductors decreases as the conductor quantity n increases. With the same quantity of conductors, in each case, the spirals whose conductors consist of seven cobalt-containing wires have a lower resistance than the spirals of the conductor device, not according to the invention, whose conductors consist of only one wire in each instance. In addition, the spirals in which one wire of the conductor consists of copper have a substantially lower resistance than the spirals whose conductors consist exclusively of cobalt-containing wires.

Of course, the copper wire could form the wire 21, i.e., the core of the conductors, rather than one of the outer wires 23. Since the core is shorter than the wires wound around it, the resistance would be somewhat lower with the same wire diameters than in the spirals according to curve 35. Moreover, one could also provide more than one copper wire, or, as mentioned before, one could provide, instead of at least one copper wire, at least one silver or possibly gold, platinum, aluminum or tungsten wire.

The fatigue resistance of spirals was also tested with the testing apparatus shown schematically in FIG. 5. The latter has a block 41 or exchangeable blocks with guide grooves extending in a U-shape, three of which are drawn and designated 41a, 41b and 41c and with which the spirals can be guided with different curvature radii, as desired. A spiral 5 to be tested is inserted in one of the guide grooves, e.g., guide groove 41a, so that the spiral is bent, by means of the semicircular part of the guide groove 41a, with the radius of curvature r. A drive apparatus 43 has a motor and a tensioning member which is rotatable around a rotational axis. The one end section of the spiral 5 projecting out of the guide groove 41a is fastened at this tensioning member in such a way that its axis coincides with the rotational axis of the tensioning member. The other end section of the spiral 5 likewise projects out of the guide groove 41a and is held with a holding and bearing device 45 so as to be freely rotatable around its axis. For the tests, the spirals are rotated around their axes at, e.g., 3000 revolutions per minute. By these means, the spirals are stressed with respect to bending, as well as torsion. Moreover, reference is made to the above-cited publication "Fatigue Performance of Stimulating Electrodes" by P. Comte et al., where this testing method is likewise discussed.

FIG. 6 contains a diagram showing some of the results of fatigue resistance tests, wherein the radius of curvature r of the spirals in millimeters is plotted on the one axis and the quantity of cycles, i.e., rotations or bendings of the spirals, designated c, is plotted on the other axis.

The two curves 47, 49 show the measurement results for spirals, each of which is formed from three conductors and has an outer diameter D of 0.8 mm. The tests were carried out with spirals without sheathings 7.

Curve 47 relates to spirals of conductor devices, not according to the invention, that is, spirals in which each of the three conductors has only a single wire with a diameter d of 0.1 mm consisting of the cobalt alloy MP 35 N.

Curve 49 relates to spirals of conductor devices, according to the invention, that is, spirals in which each of the three conductors has seven wires with a diameter d of 0.05 mm consisting of the cobalt alloy MP 35 N.

In the investigations, the quantity of cycles was determined in each case in which at least one of the conductors of the conductor devices, not according to the invention, consisting of a single wire, or at least one of the outer wires 23 of at least one conductor 11 of the conductor devices, according to the invention, was broken. The measured values designated in the curves 47, 49 by means of circles or triangles signify the number of cycles in which breakage of the type mentioned resulted. Those symbols having an arrow designate a quantity of cycles in which the measurement was terminated without breakage occurring. From similar extended time examinations of the fatigue resistance, it is known that a test specimen withstanding approximately $10^7$ cycles without breakage also usually no longer breaks with a substantially higher quantity of cycles. The symbols provided with arrows thus indicate that the spirals with the curvature radii in question practically do not break any longer.

The radius of curvature above which the spirals withstand $10^7$ cycles and thus have practically unlimited service life can be designated as critical radius of curvature. Among other things, FIG. 6 shows that the spirals of the conductor devices, according to the invention, according to curve 49, already with curvature radii from upwards of 2 mm, withstand a quantity of cycles in the order of magnitude of $10^7$ without breakage and thus have a critical radius of curvature of between 1.5 mm and 2 mm. In contrast, the spirals of the conductor devices, not according to the invention, break, according to curve 47, with a radius of curvature of 2 mm already with a quantity of cycles lying in the order of magnitude of $10^4$ and have a critical radius of curvature lying above 3 mm.

In addition, it must be noted that in the curve 47 relating to the spirals of the conductor device, not according to the invention, a measured value corresponds to the breakage of at least one of the three conductors formed by means of a single wire, wherein all three conductors usually break at the same place on the spirals. In contrast, in the curve 49 relating to the spirals of the conductor devices according to the invention, a measured value usually corresponds to the breakage of only a single one of the seven wires of one of the three conductors. Thus, in the conductor devices according to the invention, the quantity of cycles before the complete breakage of the spirals can be substantially higher still than the measured values indicated.

A substantial advantage of the tested spirals of the conductor devices according to the invention consists in that, by means of bending, they are practically exclusively elastically deformed down to very small radii of curvature in the order of magnitude of 1 mm. Accordingly, if, as can happen, e.g., during implantation, a spiral is temporarily bent with such a small radius of curvature, no permanent or lasting deformation remains after the deforming force externally applied to the spiral is removed.

Moreover, the spirals are also favorably elastically expandable in their longitudinal direction and are not sensitive to torsion.

Since silver and copper as well as other materials with high conducting ability mentioned further above have lower breaking strengths and endurance strengths than the above-mentioned cobalt alloys and stainless steel, tests were also carried out on how different kinds of breakage of a wire consisting of one of the materials with high conducting ability effects the total resistance of the spirals with conductors whose wires consist of different materials. For these investigations, in spirals whose conductors have wires consisting of a cobalt alloy and a copper wire, the latter was intentionally severed at several places. It was shown that this caused practically no increase in resistance because these interruptions are bridged over by the rest of the wires. As concerns the strength and elasticity of the spirals, the latter were also not substantially impaired through different kinds of breakage of the wires with higher conducting ability.

Accordingly, it follows from the diagrams shown in FIGS. 4 and 6 that spirals of conductor devices, according to the invention, are superior to spirals of conductor devices, not according to the invention, with identical spiral outer diameters and identical quantities of conductors, as well as with respect to the electric conductance and to the fatigue resistance.

Figure 7:
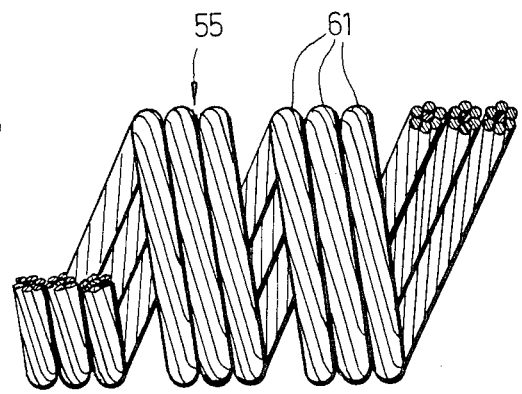
FIG. 7 is a variant of a spiral.

The somewhat simplified spiral 55 shown in FIG. 7 has adjacently extending conductors 61, e.g., three conductors 61, each of which is formed, for example, from seven stranded or interwoven wires. The spiral 55 is constructed in a manner similar to that of the spiral 5 seen in FIG. 1, but differs from it particularly in that, although the first of the three conductors contacts the second conductor and the latter contacts the third conductor, there is an open or free intermediate space between a winding of the third conductor and the adjacent winding of the first conductor.

Figure 8:
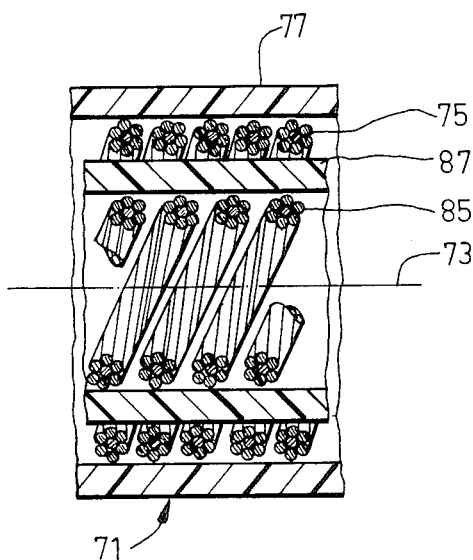
FIG. 8 is a schematized longitudinal section through a variant of a conductor device with two spirals.

FIG. 8 shows a somewhat schematized conductor device 71 which has a longitudinal axis 73, an outer spiral 75 and an inner spiral 85 which is coaxial relative to the latter. The two spirals 75, 85 can, for example, have three conductors each, each of which consists of seven wires, and can also be constructed more or less similarly to the spiral 5.

The outer spiral 75 is sheathed by an outer sheathing 77 corresponding to the sheathing 7 of the conductor device 1 and there is another sheathing 87 between the two spirals 75, 85 which consists, for example, of the same electrically insulating material as the outer sheathing 77 and insulates the two spirals relative to one another. The two spirals 75, 85 can be connected at their ends with separate contact electrodes or connections, respectively, so that the conductor device 71 forms a two-pole conductor.

In the spirals shown in FIGS. 1, 7 and 8 of the drawings, each conductor has a core formed from a wire and six wires having at least approximately the same thickness as the core wire wound or twisted around the latter and around the longitudinal axis of the conductor. However, one could also make the core wire substantially thicker than the exterior wires, for instance up to approximately five times as thick as the exterior wires. The number of exterior wires extending around the core and forming a single-layer could in that case be greater than six and range up to ten to twenty. The exterior wires can then for instance be made of the mentioned first material with a relatively high breaking strength and the thicker core wire can be formed of the mentioned second material with the relatively high electric conducting abilities. Of course, one could form the core from more than one wire also. Possibly, one could even wind only a single wire helically around the core containing at least one wire. However, it is advisable that at least two and preferably at least three wires be wound or twisted helically around the longitudinal axis and the preferably present core of the conductor, or each conductor, respectively. But the conductors can also be produced without a core and can be formed exclusively from wound or twisted together wires, respectively.

Instead of, or in addition to, winding or twisting, the wires could also be stranded in that at least one part of the wires of a conductor are braided together. If the conductor has an unbraided core, at least two wires extending in opposite directions around the core are braided together. Preferably, however, at least three or at least four wires are braided together. Of course, all wires of a conductor could also be braided together. If, at least a part of the wires of a conductor is braided, the sizes and ratios indicated previously for the winding length apply in a corresponding sense to the braid length of a conductor, i.e., the lead or pitch of the braided wires.

If the conductor has a core with at least one unwound or untwisted or unbraided wire and at least one wire wound or braided around the core, the wound wire or each of the wound or braided wires, respectively, can possibly be constructed in a band-like manner and can have a flat rectangular section or contour instead of a round profile. However, it is preferable that the wire, or each of the wires, belonging to the core have a circular cross-section.

Additionally, it would be possible to provide each conductor with a flexible sheathing which holds together the wires belonging to the conductor in such a way that they contact one another more or less but are still movable somewhat with respect to one another. When there is such a sheathing, the wires need no longer necessarily be stranded together and can possibly extend more or less parallel to one another. Such a sheathing could consist, for example, of an elastomer.

The conductor devices can not only be used as parts of heart pacemakers, but also as parts of other devices in which, within a human or animal body, either some parts of the body are to be stimulated with electric voltages and/or current or electric voltages and/or current produced by the body are to be detected. The conductor devices can either be completely inserted in the body or can be located partly within and partly outside the latter. Moreover, the spirals can be sheathed, as in the embodiment shown in FIGS. 1 and 8, with an insulating sheathing. However, it is also possible to sheathe a spiral only in the part of its length with an insulating sheathing or not to provide any such sheathing at all. In this case, a direct, electrically conducting contact between the spiral and the human or animal body part in which the spiral is inserted is possible, so that the spiral forms an actual electrode, i.e., a contact electrode.

In addition, conductor devices, according to the invention, can also be provided which are not intended for at least partial implantation in a human or animal body, but for insertion in vehicles, aircraft and rockets and other devices and mechanism in which great vibration stresses occur.

While specific embodiments of the invention have been shown and described in detail to illustrate the application of the inventive principles, it will be understood that the invention may be embodied otherwise without departing from such principles.

What is claimed is:

1. A biomedical conductor device, for at least partial insertion in a human or animal body, comprising at least one spiral formed from a plurality of electrical conductors arranged to form a single-layer winding in the manner of a multiple thread, wherein each of said conductors is formed from several wires, wherein each wire consists of the same material over its entire cross section, wherein all adjacent windings of the conductors belonging to the same spiral are in uninsulated contact with each other and wherein said conductor is constructed so as to have a rope-like configuration with at least a part of said wires being helically wound around a central axis of said conductor so that the wires belonging to the same conductor are held together and are movable with respect to each other within certain limits, said spiral being formed to define at a central inner part thereof a cavity open at one end for insertion therein of a flexible mandrel through said open end to facilitate insertion of said conductor device into said human or animal body.

2. A device according to claim 1 comprising two of said spirals, one of them enclosing the other coaxially, wherein the two spirals are separated by a sheathing of electrically insulating, rubber-elastic material.

3. A device according to claim 1, wherein said conductor has at least three wires.

4. A device according to claim 1, wherein said conductor has at least five wires.

5. A device according to claim 1, wherein said conductor has at least seven wires.

6. A device according to claim 1, wherein at least three of said wires extend around said axis of said conductor.

7. A device according to claim 1, wherein said conductor has at least one core wire forming a core, said core wire being enclosed by at least one said wire.

8. A device according to claim 7, wherein said core wire is enclosed by at least three said wires.

9. A device according to claim 7, wherein said core wire has a greater diameter than said at least one wire extending around said core wire.

10. A device according to claim 1, wherein said device has a winding length of said wires and wherein said winding length is at least 25% of the length of a winding of said conductor.

11. A device according to claim 10, wherein said winding length is at least 40% of the length of a winding of said conductor.

12. A device according to claim 10, wherein said winding length is at most 200% of the length of a winding of said conductor.

13. A device according to claim 1, wherein said wires have circular cross-sections and a wire diameter and wherein said spiral has an outer diameter, said wire diameter being at most 10% of said spiral outer diameter.

14. A device according to claim 13, wherein said wire diameter is at most 0.08 mm.

15. A device according to claim 14, wherein said wire diameter is at most 0.06 mm.

16. A biomedical conductor device, for at least partial insertion in a human or animal body, comprising at least one spiral formed from a plurality of electrical conductors arranged to form a single-layer winding in the manner of a multiple thread, wherein each of said conductors is formed from several wires, wherein each wire consists of the same material over its entire cross section, wherein all adjacent windings of the conductors belonging to the same spiral are in uninsulated contact with each other and wherein said conductor is constructed so as to have a rope-like configuration with at least a part of said wires being helically wound around a central axis of said conductor so that the wires belonging to the same conductor are held together and are movable with respect to each other within certain limits, said spiral being formed to define at a central inner part thereof a cavity open at one end for insertion therein of a flexible mandrel through said open end to facilitate insertion of said conductor device into said human or animal body, each of said conductors comprising at least one wire of a first material and at least one wire of a second material, the first of said materials having a greater breaking strength and the second of said materials having a greater electrical conductivity than the other respective material.

17. A device according to claim 16, wherein at least half of said wires of one said conductor consist of said first material.

18. A device according to claim 16, wherein at least 70% of said wires of said one conductor consist of said first material.

* * * * *